United States Patent [19]

Chodorow et al.

[11] 4,282,871
[45] Aug. 11, 1981

[54] NASO-GASTRIC TUBE STABILIZER

[75] Inventors: Ingram S. Chodorow, Upper Saddle River, N.J.; Richard Hall, New Canaan, Conn.

[73] Assignee: Technalytics Inc., Upper Saddle River, N.J.

[21] Appl. No.: 1,757

[22] Filed: Jan. 8, 1979

[51] Int. Cl.³ .................. A61M 25/02; A61M 15/08
[52] U.S. Cl. .................. 128/207.18; 128/DIG. 26
[58] Field of Search .................. 128/348-351, 128/DIG. 26, 145, 146, 147, 139, 198, 200, 206-208; 24/81 CC, 81 TH, 73 SA, 129 R, 257; 248/74 A

[56] References Cited

U.S. PATENT DOCUMENTS

| | | | |
|---|---|---|---|
| 1,981,973 | 11/1934 | Tinnerman | 24/73 SA |
| 2,831,487 | 4/1958 | Tatilaw | 128/350 R |
| 2,908,269 | 10/1959 | Cheng | 128/12 |
| 3,059,645 | 10/1962 | Hasbrouck et al. | 128/346 |
| 3,161,199 | 12/1964 | Sands | 128/206 X |
| 3,209,755 | 10/1965 | McCarthy et al. | 128/348 |
| 3,730,187 | 5/1973 | Reynolds | 128/349 R |
| 3,972,321 | 8/1976 | Proctor | 128/206 X |

*Primary Examiner*—Dalton L. Truluck
*Attorney, Agent, or Firm*—J. David Dainow

[57] ABSTRACT

A soft and flexible device with a gripping portion for releasably engaging, stabilizing and aligning the portion of a naso-gastric tube where it exits the nose adjacent a patient's upper lip; the device is releasably secured on the patient's head by an adjustable harness that encircles the head.

30 Claims, 19 Drawing Figures

NASO-GASTRIC TUBE STABILIZER

BACKGROUND OF THE INVENTION

This invention is in the field of naso-gastric tubes or stomach tubes, which are commonly used devices during and following surgery. This type of tube is typically made of clear or tinted plastic having proximal and distal ends, a central bore and additional apertures near the distal end. In use the distal end is inserted upward into a patient's nostril or mouth; then it is pushed along a path past the nasal pharynx, then downward past the oral pharynx, and finally downward through the esophagus into the stomach. At the proximal end a suction pump is connected for drainage of gastric secretions, particularly when a patient is being fed intravenously. These tubes or catheters typically remain in place from several hours to two weeks depending on the patient's condition, this device and procedure being essentially unchanged in approximately forty years. Of course there have been developed improved plastic materials which produce tubes which are stronger, smoother, self-lubricating, have x-ray opaque markings for fluoroscopic location during and after insertion, and are designed to reduce clogging.

These tubes, now made by more than one dozen manufacturers, are generally successful for their primary purpose, namely reliable drainage. However, there are numerous unpleasant, uncomfortable and sometimes dangerous ancillary effects associated with the use of these tubes or catheters, certain of these negative aspects being so familiar to surgeons and nursing staff that they have become accepted as inherent parts of procedures which require the use of naso-gastric tubes. There are two different types of problems with which we are presently concerned: (a) actual irritation, necrosis and/or ulceration of tissue associated with the nostril, pharynx, and esophagus, and (b) painful discomfort to these areas, often becoming sheer misery for the patients who must experience an indwelling naso-gastric tube or catheter during their stay in a hospital.

Certain of the problems and discomfort described above are inherent in the procedure of inserting and maintaining a naso-gastric tube in a patient's nostril; however, thereafter these problems can become aggravated by (a) bending and twisting of the otherwise stationary indwelling tube, (b) by gross movement of the tube or the patient relative to the tube, and (c) by the well-known and standard technique of using layers of adhesive tape to secure the exposed portion of the tube to the patient's upper lip or nose and cheek. Bending and twisting of the indwelling tube occurs because the downward extending exposed portion of the tube near the upper lip is bent and the tube is redirected upward past the cheek and thence to a suction apparatus. While the tube feels somewhat soft, this is misleading. In reality the tube has considerable stiffness so that it will not collapse inwardly due to the suction, and will not collapse or bend transverse to its axis while it is being pushed axially during insertion about numerous and reverse curves of the internal passageways. Thus the tube has considerable hardness and any portion of the tube bearing against tissue can lead to great pain.

Another important but subtle problem is the reaction force set up by bending this "apparently soft" tube as it exits the nostril. The edge of the nostril or other point of contact by the tube becomes a fulcrum or pivot point contacted by an intermediate portion of the tube between a lower exposed portion of the tube which is bent or pulled, and an upper indwelling portion. Specifically, if the lower part is pulled to the right, the intermediate portion remains in contact where it was, and the inward portion tends to move to the left and produce a reaction force to the left against adjacent tissue. It has been determined that this reaction force may be quite substantial.

The second of three above-listed aggravating factors in causing pain and necrosis is gross movement of the tube or the patient, as contrasted with bending and twisting a stationary tube. The tube extending out of a nostril can be moved or even yanked when the patient moves in certain improper ways, or when the sheet or other apparatus to which the tube is attached is improperly moved, or even from coughing or swallowing by the patient, with a result of severe pain in the nostril and adjacent areas.

The use of adhesive tape to reduce tube movement is only partially successful for that purpose, and such tape creates new and sometimes worse problems. The tape itself is unpleasant in that it pulls the skin constantly, is particularly uncomfortable in hot, humid conditions, and is painful to remove from the skin. Removal of the tape from the tube, when necessary, causes additional movement of the tube and associated pain. Another particularly unfortunate feature of using adhesive tape is that the tape typically holds the tube closely and tightly against the upper lip or philtrum; however, the natural direction of the tube upon exiting the nose is outward, away from the upper lip surface, and this act of adhering the tube to that surface is effectively bending the tube and causing a reaction force against other tissue upward in the nostril, as described earlier. The prior art use of additional adhesive tape to hold a portion of the naso-gastric tube tightly against the patient's cheek, leads to further pulling of the skin and bending the tube into an unnatural curvature with associated reaction forces.

Certain devices have been proposed in the prior art which engage an exposed portion of a naso-gastric tube by means of adhesive or elastic tape, or use of a sleeve or collar about the tube, while the device is secured to the head by separate tape or a harness encircling the head. This use of tape in prior devices is now considered undesirable because of the time and nuisance to secure and release the tape and the loss of effectiveness when the tape becomes wet; any requirement for wrapping elastic around the tube or sliding a collar along the length of the tube extending out of the patient's nostril either causes pain which the present invention seeks to avoid, or is too clumsy and impractical to be taken seriously. In one case a spectacle-type frame was proposed which included a clip on one temple for engaging a portion of the nasal catheter, but made no effort to align the tube properly or to prevent movement of the tube in the vicinity of the nostril. In still another unsuccessful attempt to truly solve the problems described above, an adhesive-backed VELCRO patch was adhered to the patient's cheek, and a collar with a VELCRO outer surface is secured on the tube. When pressed together the mating VELCRO surfaces will releasably adhere together; however emplacement of the collar on the tube is impractical, and the use of adhesive on the face is a procedure the present invention successfully avoids. A still further attempt to solve the above-described problems involved a device which engaged and aligned the exposed portion of a naso-gastric tube by means of slots and grooves; however, in order for the device to have sufficient strength and resilience to securely but releasably grip the tube without additional holding means, the device was made of semi-rigid material and therefore was relatively hard, and when pressed against the patient's upper lip during use, produced its own discomfort.

In reviewing all the known prior art, none of the devices solve all the problems inherent with naso-gastric tubes and inherent with the devices themselves intended to releasably locate and secure these tubes. The present invention is a device and technique which finally combine structural features to align and securely and releasably grip the tube with ease and speed, while vastly reducing patient discomfort without introducing new discomfort. More particularly, this new invention successfully reduces irritation necrosis, ulceration and pain caused by indwelling naso-gastric and related tubes, as is summarized below, followed by a detailed description of preferred embodiments of the new concept.

SUMMARY OF THE INVENTION

This invention is a device and technique for engaging a naso-gastric or other tube where it exits a patient's nose, and stabilizing the tube as regards movement in all directions. By this stabilization the tube is restrained from moving (a) axially or lengthwise further into or out of the nostril, (b) laterally toward the sides of the nostril, (c) depthwise toward the front or rear of the nose, (d) angularly by changing orientation within the nose, and (e) rotatably about its longitudinal axis. The device also reduces reaction force caused by an indwelling portion of the tube beyond the portion of the tube which is actually engaged.

In a preferred embodiment the device engages the tube in a secure but readily releasable manner, by providing a resilient gripping means which is deflectable between a first position to expose a guide surface for engaging and aligning the tube, and a second position urging the tube against the guide surface. In addition to the device gripping the tube, the device itself and captured tube are secured from moving relative to the patient's head by a harness means extending from edges of the device near the upper lip, past the cheeks, to the rear of the head or neck. The harness is of course adjustable in length and tension, to avoid creating new pressure discomfort while still holding the device and tube securely.

Another feature of the new device is its ability to grip the tube while essentially not changing the tube's natural orientation upon exiting the nose; thus we are able to greatly reduce the bending, twisting and/or pulling of the tube in the area where it exits the nose, and inward thereof where irritation and discomfort tend to be extreme with prior art naso-gastric tubes. More particularly, the preferred device allows the tube, while it extends generally downward, to remain in its normal orientation of being angled slightly sideward, toward the left cheek from the left nostril for example, and slightly forward away from the mouth, even though the remainder or proximal portion of the tube is actually redirected in an upward and lateral direction past the cheek.

A still further feature of this invention is a clip carried by the harness and situated near the patient's cheek. The clip is adapted to engage and releasably hold the portion of the tube directed past the cheek, so that adhesive tape for holding the tube to the cheek can be eliminated. In preferred embodiments the clip is pivotable, so that the tube, though gripped, can find or retain its natural orientation; this avoids one more imposed and unnatural bend in the tube and thus further reduces the sources of patient discomfort.

The device itself may take various forms within the scope of this invention, but preferably it is a soft, flexible and easily pliant material formed as a curved arch or central section having a concave surface for placement against the patient's upper lip, a front portion where a tube is releasably engaged, and means at the two ends of the central part for engaging a harness. On the front surface are one or two guide areas for receiving and properly aligning the exposed portion of the tube to coincide generally with the axis of the nostril from which the tube extends. The guide areas are dimensioned to receive a naso-gastric (sometimes abbreviated "NG") tube having diameter designated 12, 14, 16 or 18 French; a resilient means such as a separate spring cooperates with the guide area to secure the tube as so aligned, or to independently, releasably engage the tube. The act of engaging the tube along a section of defined length is an improvement over one prior art technique of gripping the tube at a single axial location which functions as a fulcrum allowing the tube to be bent above or below the fulcrum which produces an opposite reaction force in the portion of the tube beyond the fulcrum.

The central section of the base may be thicker to add firmness, however the material of the base including its ends or wings is soft and totally comfortable to the user. The material of the base may also be selected to be essentially the same as certain naso-gastric tubes made of polyvinylchloride; this will result in a very high coefficient of friction between the device and the tube which enhances the overall stabilization of the tube.

The movable spring may have exposed gripping means which are easily actuated by the patient's doctor or nurse. The movable portion of the spring that contacts the NG tube may have sharp projections that slightly pierce the surface of the tube, or at least distort the tube surface sufficiently to create a mechanical and/or frictional grip upon such surface. The NG tube has a smooth, hard, slippery surface for medical reasons, for strength requirements, and to allow easy passage through the internal body passages, and it is because of these surface characteristics that the tube-gripping means have a difficult task. Even bending the tube around obstacles helps to create mechanical and/or frictional gripping. Finally, the movable spring element can be replaced by a semi-rigid gripping element that is movable between a first position that exposes a bearing surface to receive the tube and a second position where the gripping element secures the tube in place.

As indicated above the various embodiments within the scope of this invention demonstrate the feasibility for stabilizing a naso-gastric tube in a manner which effectively reduces irritation and pain that have been almost universal problems for patients who are subjected to these indwelling naso-gastric and other tubes. Additional features of the preferred embodiment will be described below in conjunction with the drawings as follows.

DETAILED DESCRIPTION OF THE PREFERRED EMBODIMENT

Figures 1, 2, 3, 4, 5:
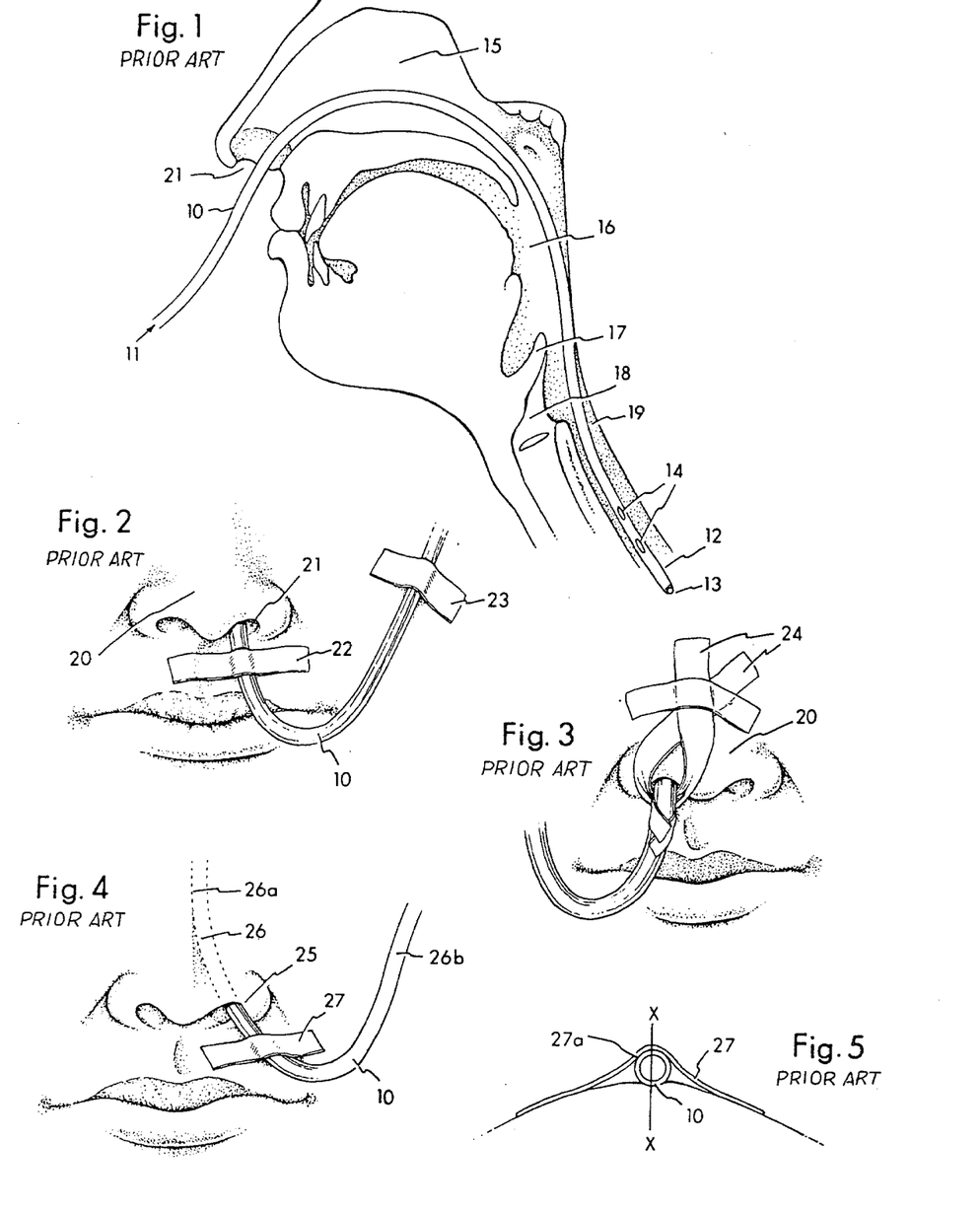
FIG. 1 is a partial mid-sagittal sectional view of a person's head.
FIG. 2 is a fragmentary front elevation view of a person's face, showing a naso-gastric tube in place.
FIG. 3 is a view similar to that of FIG. 2.
FIG. 4 is another view similar to that of FIG. 2.
FIG. 5 is a sectional view through a naso-gastric tube adhered to a patient's face with adhesive tape.

FIG. 1 shows a cross-section of a patient's head with a naso-gastric tube inserted in the normal fashion. The tube 10 has a proximal end 11 which leads to suctioning apparatus and a distal end 12, with a bore through the entire length of the tube which terminates as opening 13 and communicates with additional openings 14 at the distal end which is pushed all the way into the lowest area of the stomach. At the time of insertion the distal end starts in through the nostril at 21 and moves into area 15 designated nasal pharynx, then past areas 16 and 17 and 18 designated oral pharynx, epiglottis, and orifice to the trachea, respectively, and finally into the passage 19 leading to the esophagus.

FIG. 2 shows a front view of a patient's nose 20 with the tube 10 extending outward through a nostril marked 21, then upward leading to suctioning apparatus. Typically in the prior art, the tube 10 is maintained in place by adhesive tape 22 which may be secured to the patient's upper lip, and/or additional tape 23 secured to the patient's cheek. Another prior art adhesive tape technique as shown in FIG. 3, comprises the use of one or more strips of tape 24 from the top surface of the nose 20 downward to the portion of the tube extending out of the nose.

The adhesive tape causes general discomfort wherever it is used, and further discomfort if the tube is caused to move for one of numerous possible reasons and the tape pulls on the skin wherever it happens to be attached. There are a variety of reasons why the tube might be pulled, including mere movement of the patient relative to the proximal end, which is in the suction means, or having something touch or push the tube, such as the patient's hand or clothing, or movement of the patient's head while the rest of his body remains still. Finally, some movement of the tube may occur due to swallowing or breathing, coughing or sneezing by the patient.

A second form of discomfort and irritation caused by the tube, whether it moves or not, is pressure contact of the tube against various tissues. As can be seen, the naso-gastric tube is a bendable plastic tube which must be flexible enough to conform to the varying shapes of the passages into which it is inserted, and no two passages will be identical. The tube must also have sufficient rigidity, so that it will not collapse about a transverse axis when it is pushed axially and urged to follow the passage, and will not collapse radially when suction is applied. Consequently, it can be seen that portions of this semi-rigid tube will, where they contact portions of the body, apply some kind of pressure, which may cause actual pain, or may irritate without the patient being initially aware, leading to later tenderness or actual lesions and/or scarring. This is indicated, for example, in FIG. 4 where the tube 10 contacts the lateral edge 25 of the nostril, and where an inward portion 26 of the tube contacts the lateral wall of the medial septum.

Lateral pressure contact by part 26a of the tube, indicated in FIG. 4, is made more severe by reaction forces resulting from bending adjacent part 26b of the tube. Between parts 26a and 26b the tube is held by adhesive tape 27 which tends to operate as a fulcrum point. The tape is effective to generally hold the tube in place, however in FIG. 5, point 27a points to the very small area of actual contact of the tape 27 on the tube 10. Thus the tape restrains the tube from gross movements axailly or laterally, but in actual use the portion of the tube under the tape does pivot about an axis x—x shown in FIG. 5.

The new invention illustrated in FIGS. 6-17 provides devices which will greatly reduce the above-described pivoting movement or random movement of the tube once it is placed, will reduce pressure contact in areas where discomfort occurs, will reduce discomfort on the upper lip or cheek tissue caused by adhesive, and will reduce the compounded discomfort due to pulling of the adhesive when that occurs.

FIGS. 7-10 show a butterfly type naso-gastric tube stabilizer device 80 with a segment of tubing 81 representing a naso-gastric tube captured in this device between arm 82 of spring 83 and trough 84. This device comprises a base or central part 85 and wings 86, all being a one-piece injection molded product. For various reasons discussed later, a preferred embodiment of this device is made from a relatively soft and flexible polyvinylchloride.

Figure 6:
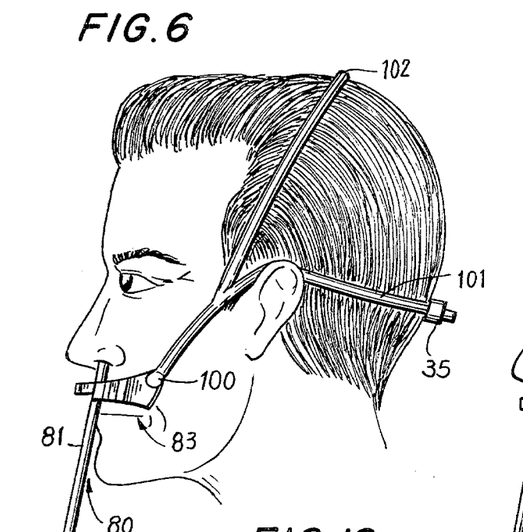
FIG. 6 is a side view of the naso-gastric tube stabilizer device positioned on a patient's head.

The device of FIGS. 7-10 is used as illustrated in FIG. 6 by placing the rear surface 87 against a patient's upper lip or philtrum, releasably securing an exposed portion of a naso-gastric tube onto the device, and releasably securing the device onto the patient's head. As shown in the Figures, the device has two troughs 84 extending from top to bottom on the front surface 88; these troughs diverge in the downward direction, and are spaced apart and angled so that a tube in a trough would be generally aligned with the axis of the corresponding nostril. Accordingly, when the exposed portion of an NG tube is secured in one of these troughs, the unexposed portion within the nasal passage remains generally aligned and unbent relative to the exposed portion, which substantially reduces the tendency of this tube to rub against and irritate sensitive tissues in the nasal passage and at its opening adjacent the upper lip. Also note each trough is angled from the upper front surface downward and further forward, away from the rear surface which completes the alignment step in positioning the troughs.

The device as a whole and particularly its rear surface are relatively soft and flexible to facilitate its conforming to the contours of the patient's upper lip and cheeks, and to thereby avoid applying pressure contact on these surfaces by any hard or sharp part of the device. The choice of soft polyvinylchloride provides another distinct advantage besides comfort. Many typical NG tubes are also made of polyvinyl-chloride which has an extremely tough and slippery surface, which leads to difficulties in firmly gripping and securing the tube to the NG stabilizer device. It has been discovered however that by forming the device of essentially the same or similar material as the tube, a rather large frictional resistance will develop between the tube and device when they are urged together. Thus, if the tube is pressed against the trough, their circumferential surfaces will be in pressure contact, and it will be difficult to slide one relative to the other. The requirement therefore is to provide releasable means for urging the tube against a trough, and this has been accomplished by the spring member 83.

The spring 83 has various structural features which cooperate with corresponding portions of the base part 85 of the NG device 80. First note that base 85 has six apertures 89 in the rear surface 87 which extend toward but do not penetrate the front surface 88. Next, there are two central apertures 90 which extend completely through the base from rear to front, and recess 91 which overlies holes 90. Spring 83 has opposite arms 82, rounded tips 93, and a central neck part 94 comprising three reverse bends 95. Near the middle of each spring arm 82 is an area 96 of perforations 97. Preferably, these perforations are formed by piercing to produce sharp or jagged edges 97A (FIG. 8) which, when urged against the tough, slippery surface of an NG tube, will engage and firmly grip that surface.

Figure 7:
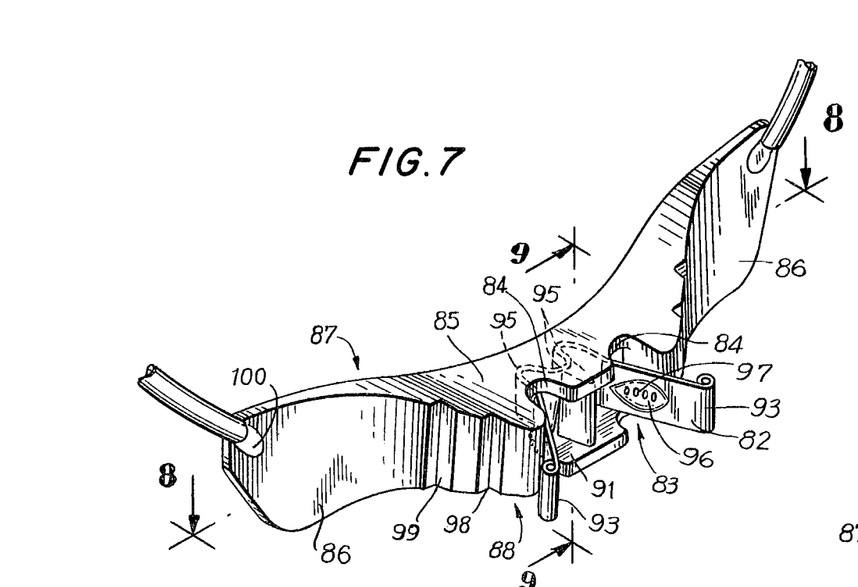
FIG. 7 is a front perspective view of the new device of FIG. 6.
Figure 8:
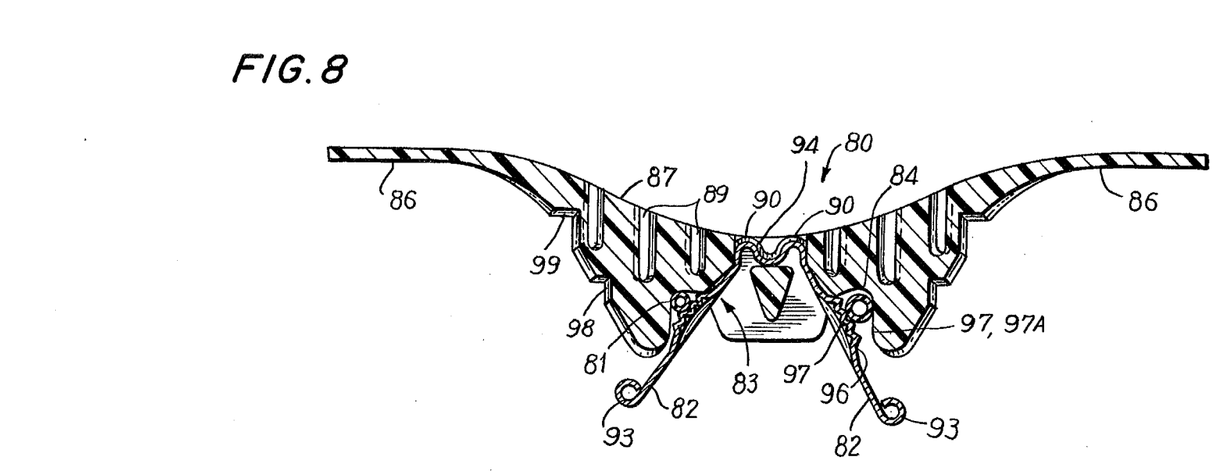
FIG. 8 is a cross-sectional view taken along lines 8—8 in FIG. 7.
Figure 9:
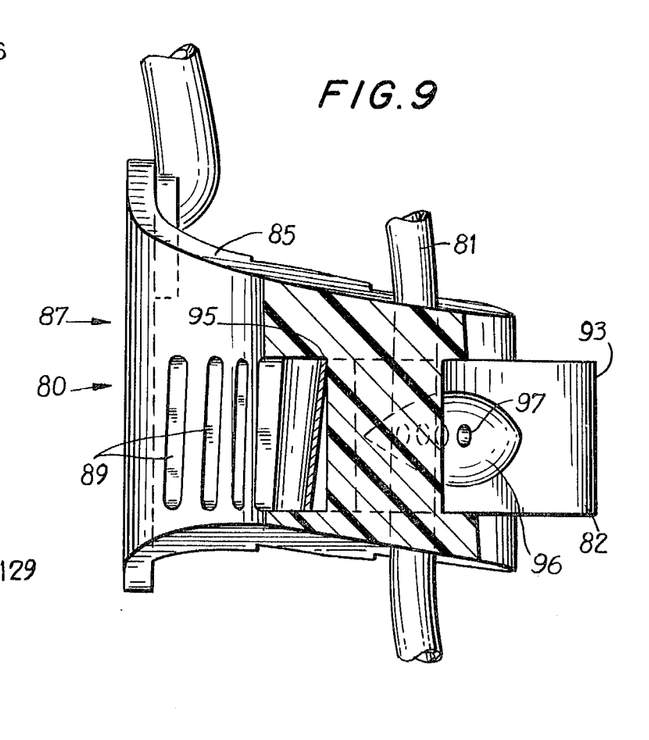
FIG. 9 is a sectional view taken along lines 9—9 of FIG. 7.

FIGS. 7 and 8 illustrate the placement of spring 83 in base 85 with the neck part 94 of the spring situated in recess 91 and spring arms 82 extending through holes 90 and through troughs 84. In the left side trough is a large diameter tube segment representing a tube-sized French 12 or 14, and in the right side trough is a small diameter tube segment representing a tube-sized French 16 or 18. It should be apparent that regardless of the tube size, the arm 82 of the spring will resiliently bend toward and against the tube, urging it tightly against the trough. The geometry and orientation of the trough will position the tube properly; the normal force of the spring will produce high frictional resistance against any sliding, i.e. axial or rolling movement of the tube relative to the trough. As discussed above, this friction will be even greater if the tube and device or trough surface are made generally of the same polyvinyl-chloride. The edges 97A of projections 97 will bite into the outer surface of the tube and add to the overall holding action of this tube-engaging means, without causing any significant damage to the tube beyond surface scratches.

The spring is preferably made of stainless steel, so that it will have the necessary properties of resilience, while being free from rust or tarnish. The spring appears to be from flat strip stock, but preferably it is rolled metal so that all exposed side edges will be rounded and smooth.

Figure 10:
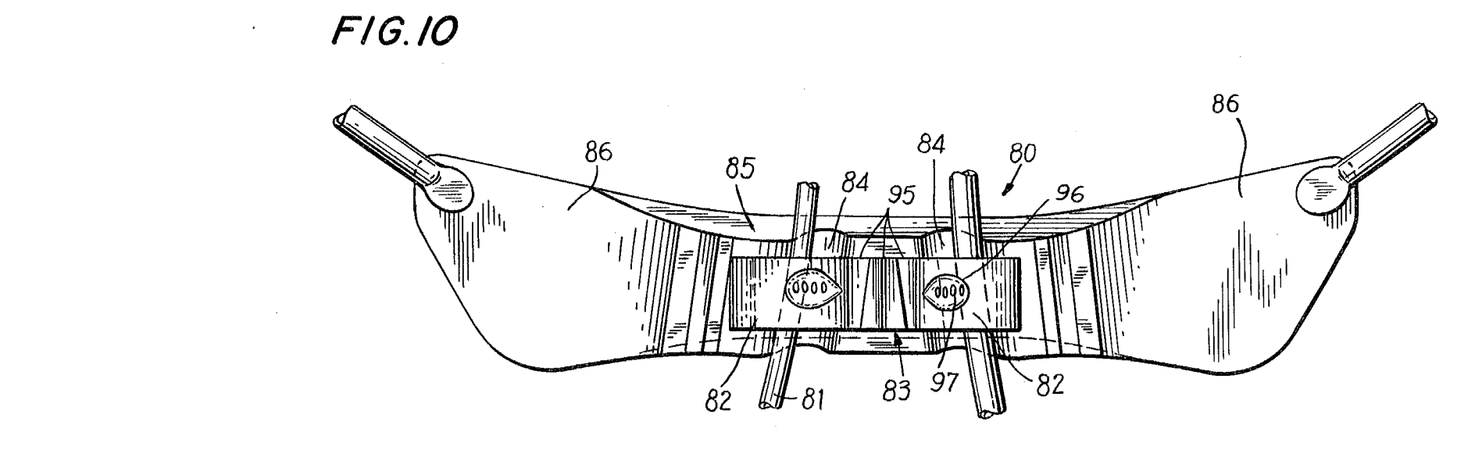
FIG. 10 is a front elevation view of the device in FIG. 9.

The curled tips 93 of the spring function as convenient handles for the surgeon or nurse to grip and squeeze toward each other in order to expose the trough to receive a portion of an NG tube. This curled aspect also makes the end edge of the spring arm inaccessible for scratching anyone or snagging on anything. As seen in FIGS. 8 and 10, the neck part 94 of the spring has the three reverse bends 95, but the axes of the bends are inclined relative to the axes of the curled arm tips 93 or to the planes of the arm 82. This inclination conforms generally to the inclination of the troughs, so that the axis of a tube in a trough is generally parallel to the plane of the arm of the spring.

The base portion 85 of this new device has two stepped areas or notches 98, 99 on each side which allow the wing parts 86 to bend around a patient's cheeks without tending to bend or move the base 85 which might alter the accurate placement and alignment of the NG tube relative to the patient's nostril. These notches thus render the side parts of the base very flexible while the central part remains sufficiently firm with the spring to securely hold the NG tube.

FIG. 7 shows a connection 100 at the edge of each wing 86 for connection to a harness as suggested in FIG. 21. There are obviously many alternatives for the end of the harness to be attached to the wing, included heat-sealing, cementing, stapling, etc. It is further desirable for the harness to have a secondary strap part 102 as shown on the basic harness strap 101. With this combination of straps, the NG stabilizer 83 will be secured from movement up, down, sideways, or forward away from the face. Strap adjustment to provide releasable variation in girth and tightness can be provided by the tubular coupling means 35 in FIG. 21 or by any other suitable device.

Figure 11:
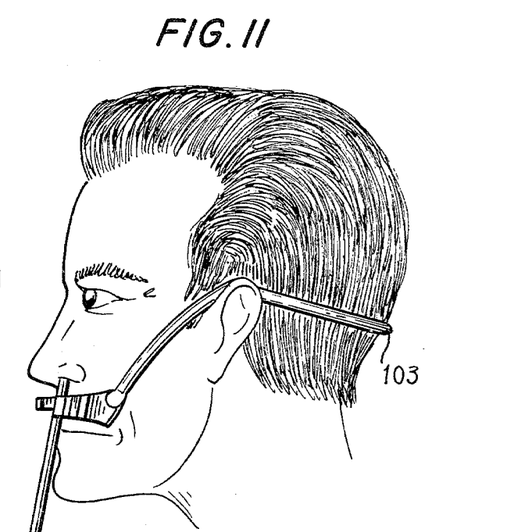
FIG. 11 is a side elevation view of the new device with a first harness configuration on a patient's head.
Figure 12:
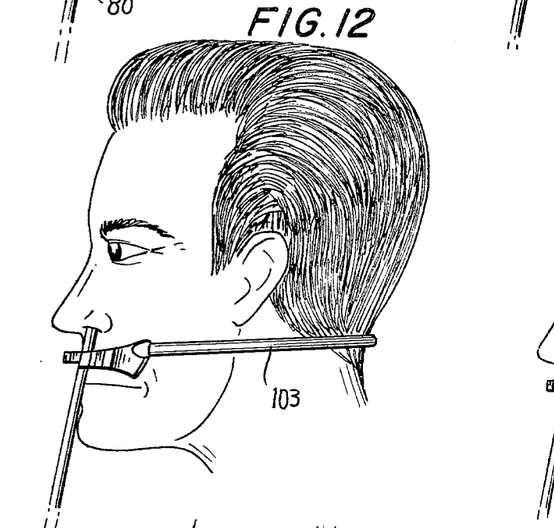
FIG. 12 shows a variation of the device and harness of FIG. 11.
Figure 13:
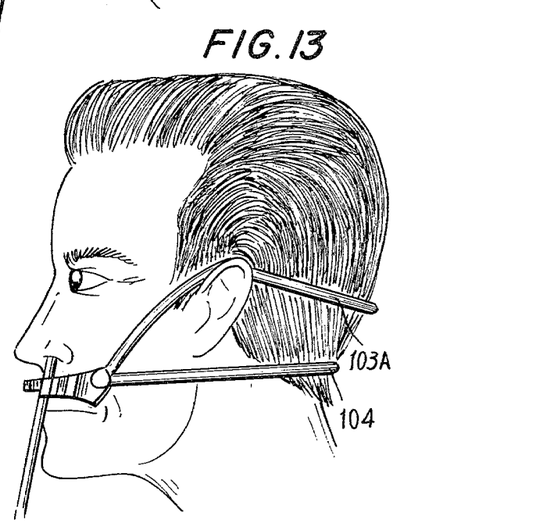
FIG. 13 is similar to FIG. 11 showing a second harness configuration.
Figure 14:
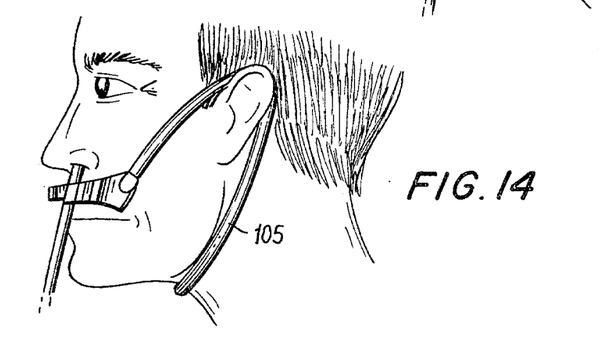
FIG. 14 is similar to FIG. 11 showing a third harness configuration.

The harness for securing the new NG stabilizer device on a patient's head may take a variety of forms in addition to the one shown in FIG. 6. The simplest form is illustrated in FIG. 11, comprising a single strap 103 extending above the ears and around the back of the head. FIG. 13 shows a variation with over-the-ear strap 103A supplemented by strap 104 extending around the neck. FIG. 14 shows a single strap 105 looped around the patient's ears and under his chin. FIG. 12 shows strap 103 below the ears.

With each strap there must be some means for varying size and tension during initial placement and for later adjustment. Elastic straps provide obvious adjustability; however it is difficult to establish the proper tension that does not later feel too tight or too loose. Also an elastic strap cannot have a fixed length that prevents displacement of the device from its proper position. It has been discovered that a strap made of polyvinyl-cholride tubing or one having similar characteristics, is soft, smooth, and comfortable on the patient's face, is easily and economically attachable to the device by heat sealing or molding integrally with the device, and is relatively inelastic, thus providing a harness which will reliably fix the position of the device after length adjustment during placement on the patient.

Figure 15:
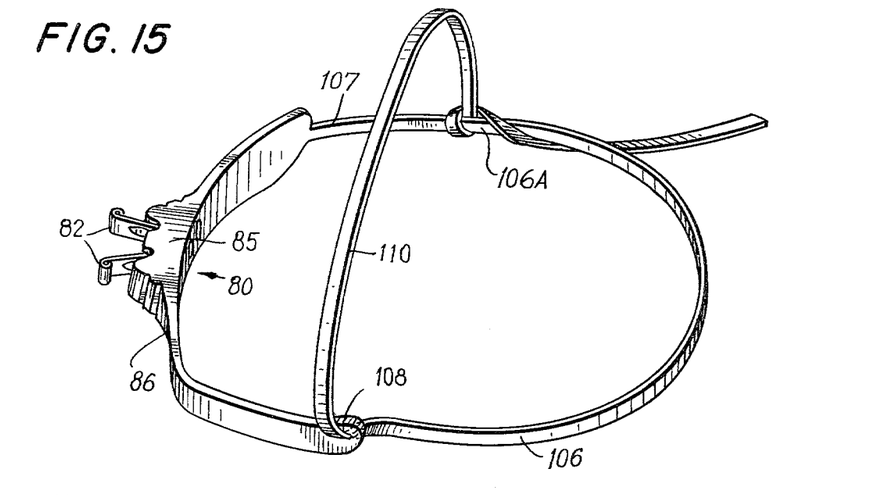
FIG. 15 shows a schematic perspective view of the naso-gastric tube stabilizer with a fourth harness configuration.
Figures 16, 17:
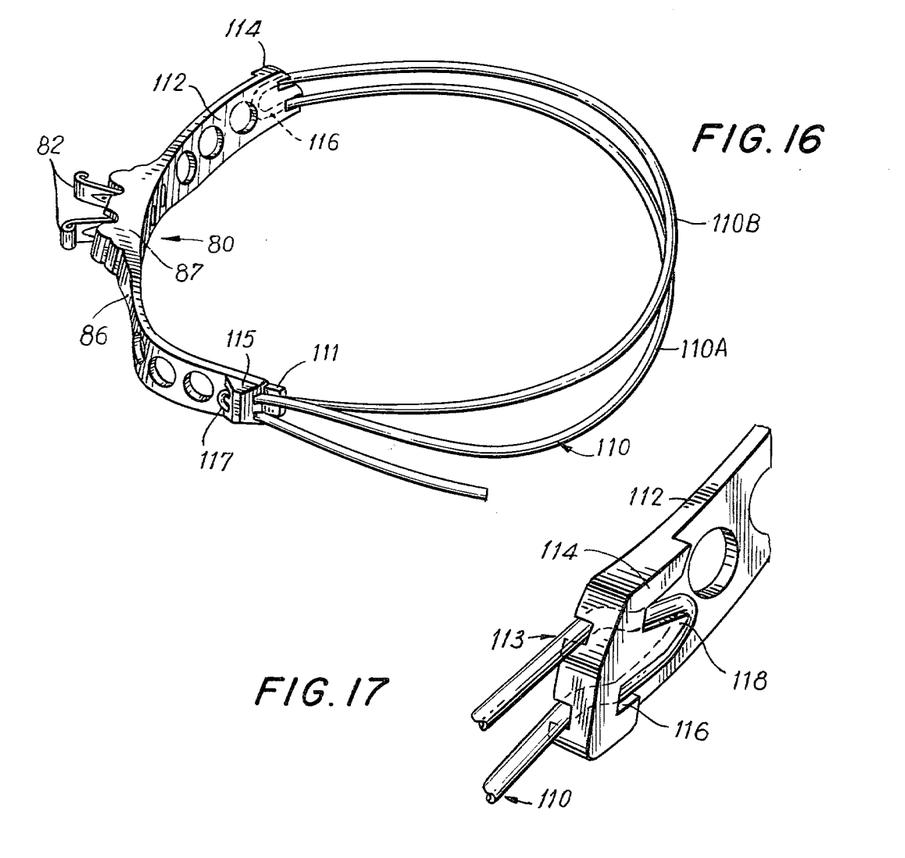
FIG. 16 is similar to FIG. 15 with a fifth harness configuration.
FIG. 17 is an enlarged fragmentary view of one end of the device of FIG. 16.

It is important for the harness to be quite simple to use and preferably to be foolproof, because complex or troublesome devices, regardless of their other fine features, will simply be avoided by hospital staff. The harness shown in FIG. 51 illustrates a single-strap concept to provide simplicity in structure and use; the harness shown in FIG. 16 is another preferred embodiment that is very practical to manufacture and easy to use. In FIG. 15 the strap 106 is permanently attached at one end 107 of the device, loops around behind the neck like strap 104 in FIG. 13, and then slides through slot 108 in the device's other end 109. The remainder of the strap 110 extends over the head like strap 103A in FIG. 13 or strap 102 in FIG. 6, and slidably engages portion 106A of the main strap 106.

In FIG. 16 the single strap 110 in secured at end 111 of the device and has a first portion 110A that extends around the patients's head to the other end 112 where it enters tunnel 113 (see enlarged view in FIG. 17). The tunnel or groove at each end of the device is in a molded block 114, 115 defining therein groove 116, and 117 respectively. Each groove is shaped to force the strap to traverse a 180° turn around nose 118, and to fit snugly, thereby developing high frictional forces that will essentially eliminate slippage. Upon exiting the groove 116 the strap portion 110B extends around the patient's head to the other groove 117 in block 115, where friction is developed similarly as in block 114. With an arrangement as disclosed herein, the single strap can be easily adjusted to provide both security and comfort, and each portion 110A and 110B of the harness can be separately adjustable. The new device as described for stabilizing a naso-gastric tube may be equally effective with other indwelling tubes which exit the nose such as esophageal, gastric, duodenal, tracheal, pharyngeal, sinusoidal, and naso-pharyngeal tubes. This device furthermore is effective to stabilize an oxygen tube which, though not indwelling, may extend from the area adjacent the upper lip into a nostril; thus a device as shown in FIG. 7-10 having two aligning, guide areas, can utilize one guide area and gripping means for a naso-gastric tube and the other for an oxygen tube.

Figure 18:
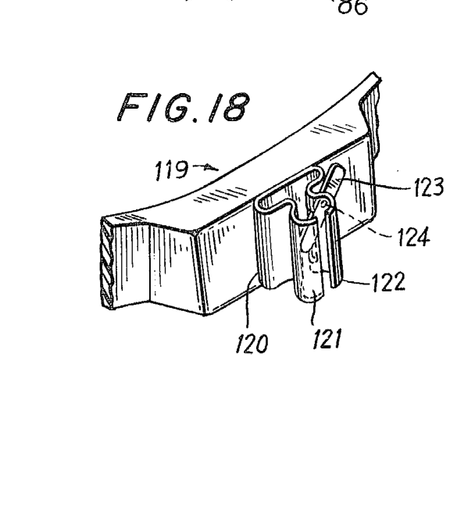
FIG. 18 is a schematic view of another embodiment of the new device.
Figure 19:
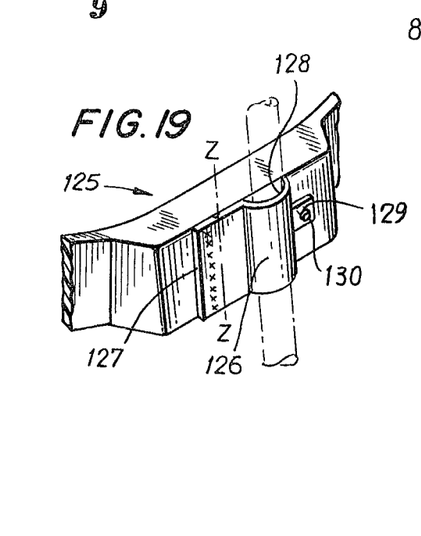
FIG. 19 is a schematic view of still another embodiment of the new device.

Until now the invention has been defined as a device for use with a standard naso-gastric tube and with spring means for resiliently urging the tube against an aligning bearing surface; this combination providing a front-loading device that may capture and release the tube easily and quickly. The spring alternatively could include its own bearing surface as suggested by the schematic view of a device 119 in FIG. 18; here spring 120 has resilient arms 121 and 122 which are normally close together, but may be separated by lever 123 which pivots about point 124 on arm 122 and drives arm 121 slightly away from arm 122. Another further embodiment within the front-loading quick-release concept is shown schematically as device 125 in FIG. 19. Clamp 126 is secured to the base along edge 127 and pivotable about axis Z—Z to expose space 128 where an NG tube can be captured. The free edge of clamp 126 includes operture 129 which engages projection 130 to releasably secure the lever in the closed tube-engaging position illustrated. The present invention could also be used to releasably secure tubes exiting other orifices of the body.

Additional variations are possible wherein the standard tube is replaced with a custom tube especially made for the device. In another case the device and tube are dimensioned to couple exactly, and they are preassembled before packaging. In another case the special tube is arranged to function also as the harness or at least as part of the harness; in this case the proximal part of the tube, after exiting the nostril and being stabilized by the new device, is directed rearward past the patient's cheek to engage with the remainder of the harness.

The embodiments described above are merely illustrative examples of the invention now defined in the claims following.

We claim:

1. A device for engaging and stabilizing an exposed section of a naso-gastric tube extending out of a patient's nostril generally along the axis thereof, the device comprising (a) a base with a central part having a front portion, a rear portion positionable adjacent the patient's upper lip, top and bottom portions, and opposite end parts, (b) first means on said central part of the base for releasably engaging and holding said exposed section of the tube, and (c) second means separate and independent of said first means for releasably securing said device to the patient's head, said first means comprising (i) a first surface on said front portion which is accessible from the front for receiving and generally aligning said tube section with the axis of the nostril when the base is adjacent the patient's upper lip, and (ii) spring means permanently secured to said base and having a gripping second surface, said spring means operable alternatively to engage and resiliently urge said tube section against said first surface and to release and allow said tube section to move axially relative to the base and to move laterally away from said base.

2. A device according to claim 1 wherein said central part has a thickness dimension in the direction of rear-to-front, said end portions comprise wings extending laterally from said central part, and said wings have a corresponding thickness dimension of a smaller magnitude.

3. A device according to claim 2 wherein each wing comprises a thin flexible strip, and said central part is firm relative to said wings.

4. A device according to claim 3 wherein said central part and wings comprise an integrally-molded unitary device.

5. A device according to claim 1 wherein said base, when oriented upright with reference to said top and bottom portions thereof, has a central vertical axis, said bearing surface defines at least one groove for receiving said portion of the naso-gastric tube, and said groove extending downward is inclined relative to said axis toward the front and toward one end portion, for defining an axis of the groove generally coincident with the axis of the patient's nostril from which said tube extends.

6. A device according to claim 5 wherein said bearing surface defines a pair of similar grooves, both inclined forward and diverging outward from each other as they descend, and said first means comprises spring means for releasably engaging a portion of a tube in each of said grooves.

7. A device according to claim 5 wherein said base's first surface has a pair of said grooves which diverge in the direction from top to bottom, and said spring means has a pair of arms situated adjacent said grooves respectively, and said central part of the spring is secured to said central part of the base.

8. A device according to claim 1 wherein said first means has a holding condition for preventing said portion of the tube from moving in any direction relative to the base, and a release condition for permitting said tube to move only axially relative to the base.

9. A device according to claim 1 wherein said spring means has sufficient force to locally, partially deform said engaged portion of said tube for securely yet releasably engaging said tube.

10. A device according to claim 1 wherein said gripping surface of the spring comprises generally sharp projections extending toward the bearing surface for engaging the surface of a tube section.

11. A device according to claim 10 wherein said gripping surface has pierced holes therein, and said projections are jagged edges of said holes.

12. A device according to claim 1 wherein said second means comprises a harness extending between said end portions of the base, said harness being adjustable in length to circumscribe a patient's head.

13. A device according to claim 12 wherein said harness comprises two separate loops for extending around the patient's neck and back of the head respectively.

14. A device according to claim 13 wherein said harness comprises a single strand.

15. A device according to claim 14 wherein said harness comprises essentially the same material as said base and is integral therewith.

16. A device according to claim 12 wherein said harness comprises generally non-elastic material.

17. A device according to claim 1 wherein said first surface has a height dimension in the top-to-bottom direction, said gripping surface of said spring means is adjacent said first surface and has a similar height dimension, whereby said tube's exposed portion is engagable along a length the same as said height dimension.

18. A device according to claim 1 wherein said spring means has a central part secured to said base of the device and at least a first arm defining thereon said gripping surface which faces said first surface for engaging and urging said tube section situated against said first surface, and first arm part being movable between a partially flexed first position where said gripping surface is closely adjacent said first surface for resiliently engaging said tube section, and a more greatly flexed second position where said gripping surface is spaced from said first surface to expose and render said first surface accessible from the front for placement and subsequent removal of said tube section, said arm part of the spring means applying a spring force toward said first surface for securing said tube section therebetween while said arm part is in either the first or second positions, or intermediate positions therebetween.

19. A device according to claim 18 wherein said spring in said first position has sufficient force to create substantial friction between said tube and the bearing surface.

20. A device according to claim 18 wherein said spring means comprises a second arm part similar but opposite to said first arm part.

21. A device for engaging and stabilizing an exposed section of a naso-gastric tube extending out of a patient's nostril generally along the axis thereof, the device comprising (a) a base with a central part having a front portion, a rear portion positionable adjacent the patient's upper lip, top and bottom portions, and opposite end parts, (b) first means on said central part for releasably engaging and holding said exposed tube section, and (c) second means for releasably securing said device to the patient's head, said first means comprising (i) a first surface on said front portion of the central part for receiving and generally aligning said exposed tube section with the axis of the nostril when the base is adjacent the patient's upper lip, and (ii) spring means secured to said base and having a gripping surface for engaging and resiliently urging said tube section against said first surface, wherein said first surface defines a pair of similar grooves, both inclined forward and diverging outward from each other as they descend, and said spring means comprises a single spring element having separate arms, each arm adjacent one of said grooves for urging a tube section against such groove.

22. A device for engaging and stabilizing an exposed section of a naso-gastric tube extending out of a patient's nostril generally along the axis thereof, the device comprising (a) a base with a central part having a front portion, a rear portion positionable adjacent the patient's upper lip, top and bottom portions, and opposite end parts, (b) first means on said central part for releasably engaging and holding said exposed section of the tube, (c) and second means for releasably securing said device to the patient's head, said first means comprising (i) a first surface on said front portion of the central part for receiving and generally aligning said exposed tube section with the axis of the nostril when the base is adjacent the patient's upper lip, and (ii) spring means which has a central part secured to said base and oppositely extending arms which define in top plan view a generally V-shape, each of said arms defining thereon a gripping surface which faces said first surface for engaging and resiliently urging a tube section against said first surface, each arm being movable between a partially flexed first position where said gripping surface is closely adjacent said first surface for resiliently engaging said tube section, and a more greatly flexed second position where said gripping surface is spaced from said first surface to expose and render said first surface accessible from the front for placement and subsequent removal of said tube section.

23. A device for engaging and stabilizing an exposed section of a naso-gastric tube extending out of a patient's nostril generally along the axis thereof, the device comprising (a) a base with a central part having a front portion, a rear portion positionable adjacent the patient's upper lip, top and bottom portions, and opposite end parts, (b) first means on said central part for releasably engaging and holding said exposed section of the tube, (c) and second means for releasably securing said device to the patient's head, said first means comprising (i) a first surface on said front portion of the central part for receiving and generally aligning said exposed tube section with the axis of the nostril when the base is adjacent the patient's upper lip, and (ii) spring means which has a central part secured to said base and oppositely extending arms, said central part comprising three continuous 180° reverse bends defining a W-shape providing substantially greater resilience than a single 180° reverse bend, each of said arms defining thereon a gripping surface which faces said first surface for engaging and resiliently urging said tube section against said first surface, each of said arms being movable between a partially flexed first position where said gripping surface is closely adjacent said first surface for resiliently engaging said tube section, and a more greatly flexed second position where said gripping surface is spaced from said first surface to expose and render said first surface accessible from the front for placement and subsequent removal of said tube section.

24. A device for engaging and stabilizing an exposed section of a naso-gastric tube extending out of a patient's nostril generally along the axis thereof, the device comprising (a) a base with a central part having a front portion, a rear portion positionable adjacent the patient's upper lip, top and bottom portions, and opposite end parts, (b) first means on said central part for releasably engaging and holding said exposed section of the tube, and (c) second means for releasably securing said device to the patient's head, said first means comprising, (i) a first surface on said front portion of the central part for receiving and generally aligning said exposed tube section with the axis of the nostril when the base is adjacent the patient's upper lip, this surface defining thereon a pair of similar grooves both inclined forward and diverging outward from each other as they descend, and (ii) spring means having a central part secured to said base, a pair of diverging arms situated adjacent said grooves respectively, and a gripping surface on each arm for engaging and resiliently urging said tube section against said first surface, said central part of the base including an aperture opening in the rear portion thereof for receiving and holding said central part of said spring.

25. A device for engaging and stabilizing an exposed section of a naso-gastric tube extending out of a patient's nostril generally along the axis thereof, the device comprising (a) a base with a central part having a front portion, a rear portion positionable adjacent the patient's upper lip, top and bottom portions, and opposite end parts (b) first means on said central part for releasably engaging and holding said exposed section of the tube, (c) and second means for releasably securing said device to the patient's head, said first means comprising (i) a first surface on said front portion for receiving and generally aligning said exposed tube section with the axis of the nostril when the base is adjacent the patient's upper lip, and (ii) spring means secured to said base and having a gripping surface for engaging and resiliently urging said tube section against said first surface, wherein said second means comprises a harness extending between said end parts of the base, said harness comprising two separate loops adjustable in length for extending around the patient's neck and back of the head respectively, and wherein each end part of the base comprises a harness-engaging coupling element which defines a curve portion of at least 180°, a portion of said harness being engagable by each curved portion, and slidable and releasably securable relative thereto for adjusting the length of said harness about a patient's head.

26. A device according to claim 25 wherein said harness comprises a strand of flexible material, and said curved portion of the harness-engaging member is a groove-like passageway.

27. A device for engaging and stabilizing an exposed section of a naso-gastric tube extending out of a patient's nostril generally along the axis thereof, the device comprising (a) a base with a central part having a front portion, a rear portion positionable adjacent the patient's upper lip, top and bottom portions, and opposite end parts, (b) first means on said central part of the base for releasably engaging and holding said exposed section of the tube, and (c) second means separate and independent of said first means for releasably securing said device to the patient's head, said first means comprising (i) a first surface on said front portion which is accessible from the front for receiving said tube section and (ii) spring means permanently secured to said base and comprising a movable arm having thereon a second surface, said spring means second surface being adjacent said first surface and movable, to engage and resiliently urge said tube section against said first surface, at least one of said first and second surfaces comprising means for generally aligning said tube section with the axis of the nostril when the base is adjacent the patient's upper lip and the tube section is engaged between said surfaces, said spring surface on said arm being movable between first and second positions respectively closely adjacent and spaced apart from said first surface, said second surface being resiliently urged toward said first surface in said first and second positions and positions therebetween.

28. A device for engaging and stabilizing an exposed section of a naso-gastric tube extending out of a patient's nostril generally along the axis thereof, the device comprising (a) a base with a central part having a front portion, a rear portion positionable adjacent the patient's upper lip, top and bottom portions, and opposite end parts, (b) first means on said central part for releasably engaging and holding said exposed section of the tube, (c) and second means for releasably securing said device to the patient's head, said first means comprising (i) a first surface on said front portion of the central part for receiving and generally aligning said exposed tube section with the axis of the nostril when the base is adjacent the patient's upper lip, and (ii) spring means which has a central part secured to said base and at least one arm having a gripping surface which faces said first surface for engaging and resiliently urging a tube section against said first surface, said arm being movable between a partially flexed first position where said gripping surface is closely adjacent said first surface for resiliently engaging said tube section, and a more greatly flexed second position where said gripping surface is spaced from said first surface to expose and render said first surface accessible from the front for placement and subsequent removal of said tube section.

29. A device for engaging and stabilizing an exposed section of a tube extending out of a patient's body orifice generally along the axis thereof, the device comprising (a) a base with a central part having a front portion, a rear portion positionable adjacent the patient's body, top and bottom portions, and opposite end parts, (b) first means on said central part of the base for releasably engaging and holding said exposed section of the tube, and (c) second means separate and independent of said first means for releasably securing said device to the patient's body, said first means comprising (i) a first surface on said front portion which is accessible from the front for receiving and generally aligning said tube section with said axis when the base is adjacent the patient's body, and (ii) spring means permanently secured to said base and having a gripping second surface, said spring means operable alternatively to engage and resiliently urge said tube section against said first surface and to release and allow said tube section to move axially relative to the base and to move laterally away from said base.

30. A device for engaging and stabilizing an exposed section of a naso-gastric tube extending out of a patient's nostril generally along the axis thereof, the device comprising a base with a central part having a front portion, a rear portion positionable adjacent a patient's upper lip, top and bottom portions, and opposite end parts, first means on said central part for releasably engaging and holding said exposed section of the tube, and second means separate and different from said first means for releasably securing said device to the patient's head, said first means comprising (i) a first surface on said front portion for receiving and generally aligning said tube section with the axis of the nostril when the base is adjacent the patient's upper lip, and (ii) spring means secured to said base and having a second surface, said spring means operable alternatively to have its second surface engage and resiliently urge said tube section against said first surface or to release said tube section from said base.

* * * * *